United States Patent
Cho et al.

(10) Patent No.: US 8,934,089 B2
(45) Date of Patent: Jan. 13, 2015

(54) ELECTROLUMINESCENCE SAMPLE ANALYSIS APPARATUS

(71) Applicant: Dongguk University Industry-Academic Cooperation Foundation, Seoul (KR)

(72) Inventors: Hoon Young Cho, Gyeonggi-do (KR); Dong Wha Lee, Seoul (KR); Dong Wook Kwak, Gyeonggi-do (KR); Hyun Yul Choi, Gyeonggi-do (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 99 days.

(21) Appl. No.: 13/660,765

(22) Filed: Oct. 25, 2012

(65) Prior Publication Data

US 2013/0057862 A1    Mar. 7, 2013

Related U.S. Application Data

(63) Continuation of application No. PCT/KR2011/002250, filed on Mar. 31, 2011.

(30) Foreign Application Priority Data

May 6, 2010  (KR) .................. 10-2010-0042633

(51) Int. Cl.
*G01N 21/00* (2006.01)
*G01N 21/66* (2006.01)

(52) U.S. Cl.
CPC .................................. *G01N 21/66* (2013.01)
USPC ........................................................ 356/73

(58) Field of Classification Search
CPC .......................................................... G01J 3/02
USPC ........................................................ 356/73
See application file for complete search history.

(56) References Cited

U.S. PATENT DOCUMENTS 3,859,595 A    1/1975    Lang
6,331,438 B1    12/2001    Aylott et al.
(Continued)

FOREIGN PATENT DOCUMENTS

JP    2008026113 A    2/2008
JP    2010071874 A    4/2010
KR    100924491 B1    11/2009

OTHER PUBLICATIONS

EPO Search Report dated Oct. 10, 2013, received in related EP Patent Application No. 11777502.3, 5 pgs.
(Continued)

*Primary Examiner* — Tarifur Chowdhury
*Assistant Examiner* — MD Rahman
(74) *Attorney, Agent, or Firm* — Grossman Tucker Perreault & Pfleger, PLLC

(57) ABSTRACT

Provided is an apparatus for analyzing an electroluminescence sample, which comprises: a pulse generator for applying a pulse driving signal to the electroluminescence sample; an electroluminescence (EL) detector for receiving electroluminescence which is emitted from the electroluminescence sample according to the application of the pulse driving signal, thereby acquiring a light-receiving signal; a temperature controller for varying the temperature of the electroluminescence sample; and an electroluminescence transient spectroscopy (ELTS) analysis unit for analyzing a change in a time division section of the light-receiving signal delayed depending on a change of the temperature of the electroluminescence sample, and acquiring information on a defect-type charge trap which exists in the electroluminescence sample.

13 Claims, 6 Drawing Sheets

(56) References Cited

U.S. PATENT DOCUMENTS

| | | | |
|---|---|---|---|
| 7,446,868 B1 | 11/2008 | Higgs et al. | |
| 7,847,237 B2 | 12/2010 | Fuyuki | |
| 8,004,270 B2 | 8/2011 | Kasahara et al. | |
| 2002/0090650 A1* | 7/2002 | Empedocles et al. | 435/7.1 |
| 2004/0106211 A1* | 6/2004 | Kauer et al. | 436/169 |
| 2008/0007267 A1* | 1/2008 | Prelas et al. | 324/452 |

OTHER PUBLICATIONS

Lang, D.V., "Deep-level transient spectroscopy: A new Method to characterize traps in semiconductors", Journal of Applied Physics, vol. 45, No. 7, Jul. 1974, pp. 3023-3032.

Versluys, Clauws P. et al., "Characterization of deep defects in Cds/CdTe thin film solar cells using deep level transient spectroscopy", Science Direct, Thin Solid Films vol. 451-452, pp. 434-438, Mar. 2004.

"International Preliminary Report on Patentability", International Preliminary Report on Patentability with Written Opinion issued Nov. 6, 2012, received in corresponding PCT Application No. PCT/KR2011/002250, 6 pgs. (English language translation).

"International Search Report", International Search Report mailed Dec. 7, 2011, received in corresponding PCT Application No. PCT/KR2011/002250, 2 pgs. (English language).

English language translation of Chinese Office Action issued Mar. 25, 2014, received in related Chinese Application No. 201180022720.2, 5 pgs.

* cited by examiner (a)

(b)

(a)

(b)

ELECTROLUMINESCENCE SAMPLE ANALYSIS APPARATUS

CROSS-REFERENCE TO RELATED APPLICATIONS

This application is a continuation of PCT/KR2011/002250 filed Mar. 31, 2011, which claims the benefit of Korean Patent Application No. 10-2010-0042633, filed with the Korean Intellectual Property Office on May 6, 2010, the disclosure of which is incorporated herein by reference in its entirety.

TECHNICAL FIELD

The present invention relates to an apparatus for inspection and analysis, more specifically to an apparatus for analysis of an electroluminescence (EL) sample.

BACKGROUND ART

A solar cell, which is a semiconductor device that converts solar energy to electric energy, has the junction forms of a p-type semiconductor and an n-type semiconductor and has the same basic structure as a diode. When light is incident at a semiconductor, an interaction occurs between the absorbed light and materials constituting the semiconductor. Then, electrons, which have negative charges and positive charges, and positive holes (where electrons are missing) are generated, allowing the electric current to flow or generating electricity. This is referred to as the photoelectric effect. There are two types of semiconductors, one being n-type semiconductors, which attract electrons having a negative charge, and the other being p-type semiconductors, which pull positive holes having a positive charge. The solar cell has these two types of semiconductors joined together. Generally, the negative charges generated in the semiconductor are pulled toward the n-type semiconductor, and the positive charges are pulled toward the p-type semiconductor. Accordingly, the negative charges and the positive charges are gathered, respectively, at either electrode. By connecting both electrodes with an electric wire, electricity flows, and electric power can be obtained. Here, the numbers of the positive charges and the negative charges become the same. Accordingly, power becomes continuously generated as long as there is light. That is, once light is incident, an interaction between the light and the materials occurs within the semiconductor to generate the positive charges and the negative charges, and electricity is flowed by discharging the charges to the outside, allowing the electric energy to operate a motor or turn on a light. Accordingly, the solar cell can covert not only the sunlight but also the light from a fluorescent lamp to electricity.

Solar photovoltaic power generation systems, which utilize solar cells, are expected to provide at least one of the solutions for the environmental problems and the energy problems caused by the global warming, and the solar photovoltaic power is expected to provide about 70% of the world energy in 2100. One of the most important issues for realizing the energy vision is the improvement of energy conversion. While crystalline Si solar cells takes up about 90% of the entire solar cell production, their efficiency, which is currently about 24.7%, is limited to improve up to 29%, and thus it is difficult to expect a dramatic improvement of the efficiency. The efficiency of 40.8% has been achieved owing to condensing operation of solar cells having a 3-junction structure of InGaP/InGaAs/Ge based on the III-V compound semiconductor technology, and an ultrahigh efficiency of over 50% is expected through multi-junctions, such as 4-junction, 5-junctions, etc.

An LED (light emitting diode) uses the process of emitting light (light-emitting recombination of electron-hole) while electrons of the semiconductor in a conduction band, which is an excited state, move to a valance band, which is a ground state. Used for practical LEDs are compound semiconductors, of which the band gap structure is a direct transition type. This is because a high probability of light-emitting recombination is achieved only if the momentum of electrons at a bottom of the conduction band and the momentum of the positive holes at a top of the valence band are almost the same. The light emitting color of the LED is determined by the energy band gap of the semiconductor materials constituting an active layer (i.e., light-emitting area). The band gap of GaAS is about 1.43 eV and emits a near infrared ray of 870 nm. A visible light LED uses a material having a greater energy band gap. Used for a high efficiency LED is a multi-layer film that is fabricated through epitaxial growth of a plurality of compound semiconductor films, which have different energy band gaps from one another. For materials for the board, GaAS (infrared ray~visible light) or GaP (visible light) is used, and sapphire ($Al_2O_3$) or silicon carbide (SiC) is used for blue light to ultraviolet ray.

During the early days of LED development, a simple p-n junction was used. The n-type area or p-type area that is close to a depletion layer was used as a light-emitting junction layer. This is an area containing impurities, and thus it was difficult to obtain a high efficiency LED. The most general way to improve the light-emitting efficiency is a double-hetero (DH) structure, in which the band gap of the p-type and n-type areas is made to be greater than the band gap of the active layer. While enhancing the effect of confining the electrons and the positive holes in a quantum-well structure by making the active layer thinner, it has been attempted to improve the density of electron state at an end of the band. The rate of optical power for an electric current put into the LED (i.e., external quantum effect) is determined by an efficiency of emitting the light from a chip and a light-emitting recombination ratio (i.e., internal quantum effect) excluding a Joule loss by series resistance including the electrodes. An LED includes a board and electrodes, by which some of the light generated by the active layer is absorbed. It is preferable that a band gap of the board material is bigger than a band gap of the active layer. Studies are currently underway for problems of surface ruggedness and deteriorated efficiency caused by mold materials, in addition to semiconductor materials.

As one of the inherent problems that must be solved for solar cells and LED devices, defective charge traps affect the operation characteristics, when the device is operated, by changing the operation conditions as active electrons and holes are captured. Accordingly, in order for such a device structure to take its place as a next generation device, device characteristics with reproducibility and durability are required, and systematics studies are required not only for thin films, which are still not solved, but also for the process of capturing the electrons and holes in a multi-layer structure, the distribution and structure of the traps in an optically-activated multi-layer structure, and energy distribution.

In the case of the trap that is present in the solar cell and the LED structure, the quantity of traps that can capture the charges is relatively increased compared to its size, and the trap is present in various energy levels. In the case of a poly crystalline structure of device thin film, it is deemed that there could be more traps in addition to the reported defective trap, but there is no analysis method that can cover all of the defective traps due to the limitations of energy band gap of the material, and the scope of observable trap is limited if one analysis technology is used. Moreover, an interface defective trap between layers that is deemed to be surely present is expected to affect operation characteristics of the device, and thus the importance of method of analyzing the surface and interface cannot be neglected. Accordingly, it is expected in the photoelectric device that the interface trap (IT) and the surface trap (ST), as well as the charge trap (CT), will affect the charge separation and its operation life in the structure because, the solar cells, which are exposed to outside environment unlike other devices, are more affected by the defective traps with an increased time. Therefore, by analyzing the precise origin of the charge trap and tracking and controlling its cause, it will be possible to make a contribution to the currently-demanded low-cost, high-efficiency solar cell and LED device.

Studies for analysis of non-destructive charge traps using principles of photo-electronic physics such as ELTS will be imperative for verification of a wide range of traps and evaluation of device performance in the area of next-generation solar cells and LED.

SUMMARY

The present invention provides an apparatus for analysis of an electroluminescence sample that can verify information about distribution, structure and energy distribution of defective charge traps that are present within an EL emission device such as a solar cell and LED.

The present invention also provides an apparatus for analysis of an electroluminescence sample that can integrally analyze information on lifetime of an EL emission device and an EL image as well as information on the defective charge trap through one analysis apparatus.

The present invention also provides an apparatus for analysis of an electroluminescence sample that can photograph and provide an EL image in micro units for verification of surface defect of an EL emission device.

An aspect of the present invention features an apparatus for analysis of an electroluminescence sample including: a pulse generator configured for applying a pulse driving signal to the electroluminescence sample; an electroluminescence (EL) detector configured for acquiring a light-receiving signal by receiving electroluminescence emitted from the electroluminescence sample as a result of application of the pulse driving signal; a temperature controller configured for varying the temperature of the electroluminescence sample; and an electroluminescence transient spectroscopy (ELTS) analysis unit configured for acquiring information on a defective charge trap existing in the electroluminescence sample by analyzing a change in a transient section of the light-receiving signal according to a temperature change of the electroluminescence sample.

In one embodiment, the pulse generator can generate a square wave pulse in correspondence with temperature change of the electroluminescence sample by the temperature controller, and the EL detector can detect EL emitted from the electroluminescence sample in response to the square wave pulse when the square wave pulse is applied.

In one embodiment, the light-receiving signal obtained by the EL detector can be one of a photo current signal, a photo voltage signal and a capacitance signal.

The ELTS analysis unit can obtain at least one of information about an activation energy level of the defective charge trap, a concentration of the defective charge trap and a capture cross-section of the defective charge trap by sampling two time points in the transient section of the light-receiving signal, calculating a difference of the light-receiving signal at the two sampled time points, and using a relation of change in the difference of the light-receiving signal according to the temperature change.

The ELTS analysis unit can further obtain lifetime information by analyzing the transient section of the light-receiving signal obtained at a fixed temperature, and the lifetime information can be at least one of information about a minority carrier and the defective charge trap and can be obtained by calculating a time constant of the transient section that changes exponentially.

The apparatus for analysis of an electroluminescence sample in accordance with an embodiment of the present invention can also include: a photographing device configured for obtaining an EL image for EL emitted from the electroluminescence sample; and a surface defect analysis unit configured for analyzing a surface defect of the electroluminescence sample based on the EL image.

A microscope can be positioned in front of the photographing device on an optical path of the EL, and the surface defect analysis unit can analyze the surface defect of the electroluminescence sample based on the EL image in micro units obtained from the photographing device.

The apparatus for analysis of an electroluminescence sample in accordance with an embodiment of the present invention can also include an optical separator configured for optical separation in such a way that some of the EL emitted from the electroluminescence sample is inputted to the EL detector and the other is inputted to the microscope.

The apparatus for analysis of an electroluminescence sample in accordance with an embodiment of the present invention can also include a spectroscope configured for detecting a desired wavelength only or cut off an undesired wavelength of EL light emitted from the electroluminescence sample.

EFFECT OF INVENTION

An embodiment of the present invention can provide an apparatus for analysis of an electroluminescence sample that can verify information about distribution, structure and energy distribution of defective charge traps that are present within an EL emission device such as a solar cell and LED.

An embodiment of the present invention can also integrally obtain information on lifetime of an EL emission device and an EL image as well as information on the defective charge trap, saving time and cost for testing and analyzing the EL emission device.

An embodiment of the present invention can also photograph and provide an EL image in micro units for verification of surface defect of an EL emission device, improving the reliability and accuracy of the surface defect test.

An embodiment of the present invention can also analyze and measure the information on the defective charge trap and the information on the lifetime of the minority carrier for an apparatus that is integrated in an end product.

DETAILED DESCRIPTION

Since there can be a variety of permutations and embodiments of the present invention, certain embodiments will be illustrated and described with reference to the accompanying drawings. This, however, is by no means to restrict the present invention to certain embodiments, and shall be construed as including all permutations, equivalents and substitutes covered by the ideas and scope of the present invention.

Throughout the description of the present invention, when describing a certain technology is determined to evade the point of the present invention, the pertinent detailed description will be omitted. Moreover, numerals (e.g., first, second, etc.) in the description of the present invention are used only to distinguish one element from another.

When one element is described as being "connected" or "accessed" to another element, it shall be construed as being connected or accessed to the other element directly but also as possibly having another element in between unless otherwise specified.

Hereinafter, an apparatus for analysis of an electroluminescence sample in accordance with an embodiment of the present invention will be described with reference to the accompanying drawings.

Figure 1:
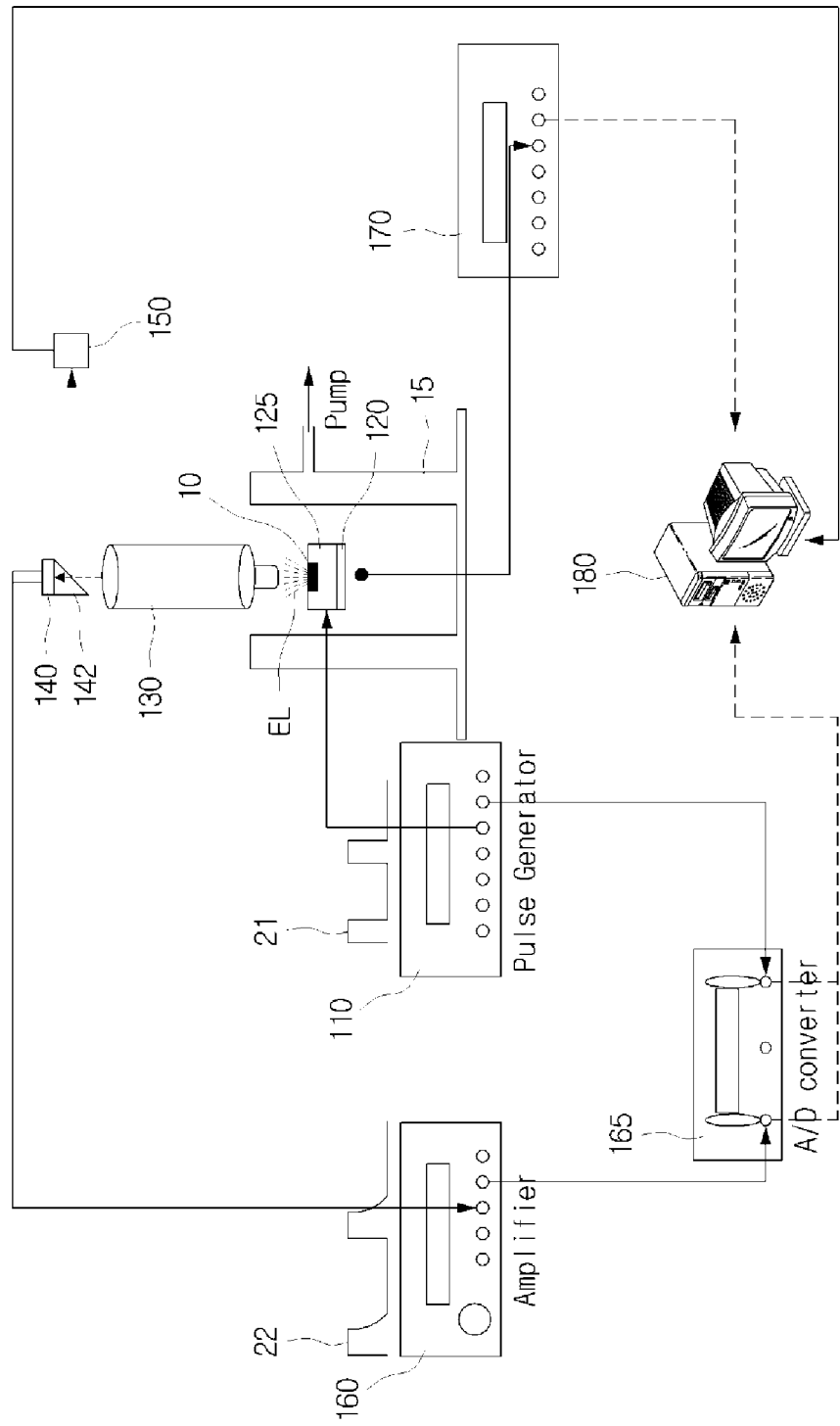
FIG. 1 shows a brief configuration of an apparatus for analysis of an electroluminescence sample in accordance with an embodiment of the present invention.

FIG. 1 shows a brief configuration of an apparatus for analysis of an electroluminescence sample in accordance with an embodiment of the present invention.

Referring to FIG. 1, the apparatus for analysis of an electroluminescence sample in accordance with an embodiment of the present invention can include a vacuum chamber 15, a pulse generator 110, a temperature controller 120, a microscope 130, an optical separator 142, an EL detector 140, a photographing device 150, an amplifier 160, an A/D converter 165, temperature detection and control unit 170, an analysis unit 180, etc. As the elements illustrated in FIG. 1 are not essential, it is possible to realize an electroluminescence sample analysis apparatus having more or fewer elements depending on how it is designed.

By including the above elements, the electroluminescence sample analysis apparatus of the present invention can be utilized as an apparatus having three functions, namely, an ELTS (Electroluminescence Transient Spectroscopy) analysis apparatus, an electroluminescence lifetime analysis apparatus, and a near-infrared image analysis apparatus in an area of micro units. Hereinafter, these three functions of the electroluminescence sample analysis apparatus will be described one by one.

ELTS Analysis Apparatus

An electroluminescence sample 10 can be mounted in a mount member 125 and placed in the vacuum chamber 15. Here, the pulse generator 110 generates and applies a pulse driving signal (a square wave pulse 21 in this example) to the electroluminescence sample 10 in the vacuum chamber 15.

Once the pulse driving signal is applied as described above, the electroluminescence sample 10 emits an EL light. For example, in the case of an LED, an EL light in a pertinent color region (i.e., a pertinent wavelength band) can be emitted, and in the case of a solar cell, an EL light in a near-infrared region can be emitted.

Here, the principle of emitting EL is as follows. EL (electroluminescence) refers to an optical, electrical phenomenon that emits light as a result of recombination of charge carriers having different symbols, i.e., electrons and holes, when a strong electric field is formed or electric current flows through a material (generally, a semiconductor). In order to obtain the EL light, it is necessary to bring the electrons inside a crystal lattice to a higher energy level. Here, the light-emitting intensity depends on a defect density of the sample, and the fewer the defects are, the more photons are emitted.

In FIG. 1, the apparatus is configured in such a way that the EL light emitted from the EL sample 10 is passed through the microscope 130 and then permeates through the optical separator 142 before being received by the EL detector 140. However, this is merely an example of how the analysis apparatus in accordance with the present invention is configured so as to realize both the functions of the ELTS analysis apparatus and an EL image obtaining apparatus for analysis of surface defect in micro units.

Therefore, it shall be apparent that the apparatus can be designed differently from the configuration shown in FIG. 1 while the above-described two functions are simultaneously realized. In the case of FIG. 1, some (i.e., permeated light) of the EL light inputted to the microscope 130 is received by the EL detector 140 through the optical separator 142, and the other (i.e., reflected light) is received by the photographing device 150, such as a CCD camera, but there can be different ways to design this configuration. For example, the optical separator 142 can be placed at a front end (optical input end) of the microscope 130, instead of a read end (optical output end) of the microscope 130. In such a case, the photographing device 150 will receive the EL light having passed through the optical separator 142 and the microscope 130, but the EL detector 140 will receive the EL light having passed through the optical separator 142 only. Moreover, the microscope 130 and the EL detector 140 can be respectively placed where the EL light emitted from the EL sample 10 can be directly received, in which case the optical separator 142 can be omitted from the configuration.

Although it is illustrated in FIG. 1 that the EL light emitted from the EL sample 10 passes through the microscope 130 and then is received by the EL detector 140 or the photographing device 150, this is only an illustrated example, and it is also possible that the EL light emitted from the EL sample 10 is received by the EL detector 140 or the photographing device 150 without passing through the microscope 130. In addition, although it is illustrated that the EL light received by the EL detector 140 then passes through the amplifier 160, this is also only an illustrated example, and it is possible to omit the amplifier 160 from the configuration. Meanwhile, it is possible to receive the EL light through a spectroscope (not shown), which separates a particular wavelength of the EL light emitted from the EL sample 10. Here, the spectroscope can use, for example, a filter to receive a desired wavelength or cut off an undesired wavelength.

Afterwards, a light-receiving signal detected through the EL detector 140 can be sent to the analysis unit 180 through the amplifier 160 and the A/D converter 170, as illustrated in FIG. 1. Here, the EL detector 140 can be a photo diode or a photo detector, and the light-receiving signal obtained through the EL detector 140 can be a photo current signal, a photo voltage signal or a capacitance signal corresponding to the intensity of the EL light.

In an ideal case (that is, when there is no defect in the EL sample 10), the light-receiving signal obtained from the EL detector 140 will have a same wave form as the inputted pulse driving signal but, in reality, will have a wave form with transient sections, as illustrated by reference numeral 22 in FIG. 1.

Since such a deformation in the wave form of the light-receiving signal is caused by the defect that is present in the EL sample 10, it is possible to obtain the information about the defect that is present in the EL sample 10 by analyzing the transient sections of the light-receiving signal. This will be described below with reference to FIG. 2 to FIG. 4.

Figure 2:
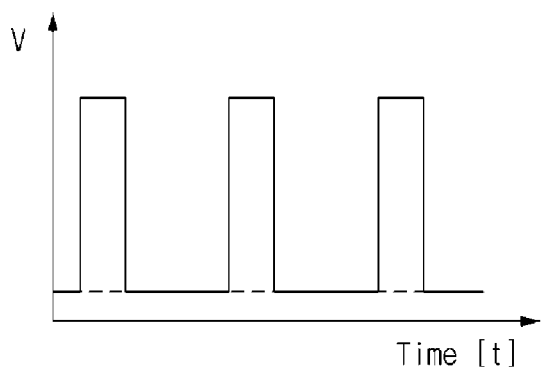
FIG. 2 illustrates pulse driving signals applied to an electroluminescence sample and a photo current as a light-receiving signal having received EL emitted from the electroluminescence sample.
Figure 2:
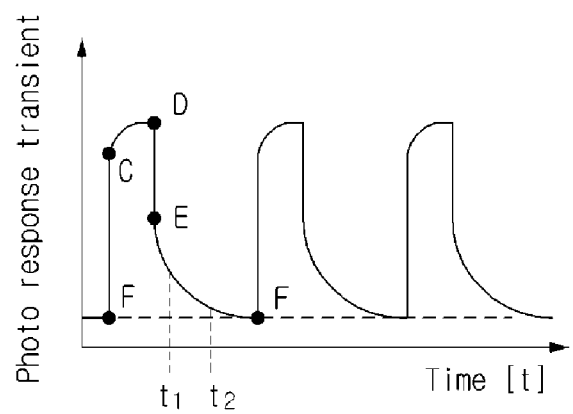

FIG. 2 illustrates pulse driving signals applied to an electroluminescence sample and a photo current as a light-receiving signal having received EL emitted from the electroluminescence sample.

For ELTS measurement, once the pulse driving signal, such as the one shown in (a) of FIG. 2, is applied to a junction of the EL sample 10 through the pulse generator 110, the EL detector 140 senses the EL light emitted from the EL sample 10 to obtain the light-receiving signal according to a response function (current, voltage or capacitance) of the EL detector 140. Here, the light-receiving signal can be like the one shown in (b) of FIG. 2.

In (b) of FIG. 2, in the case that the response function of the EL detector 140 is a photo current, the F~C section is where a photo carriers of the EL detector 140 are generated by photo excitation of the sample and the detector current is suddenly increased, and the C~D section is where the photo carriers generated in the F~C section are captured in the trap and maintained in a quasi-steady state. The D~E section is where the current is decreased again by recombination of the photo carriers. Lastly, the E~F section is where the photo carriers captured in the trap are de-trapped by thermal energy, wherein the current here has a transient curve.

Figure 3:
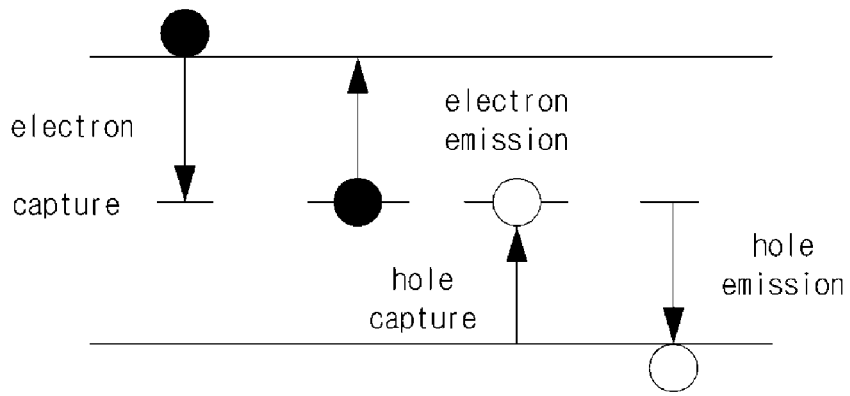
FIG. 3 illustrates a process of capturing and discharging a carrier and the carrier captured in a trap.
Figure 3:
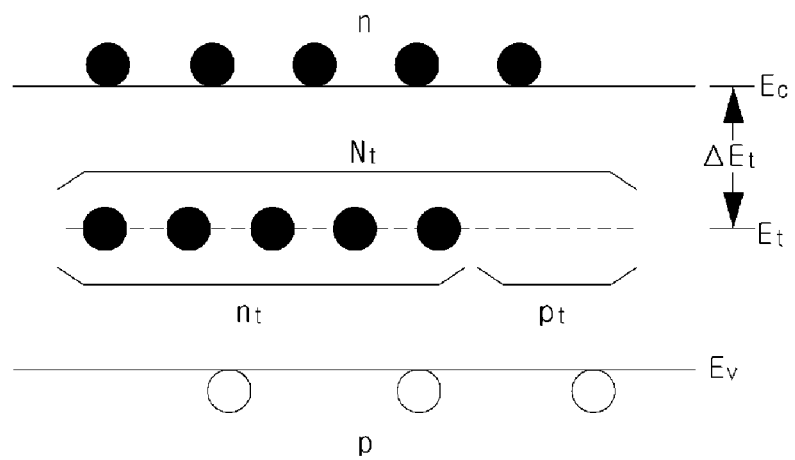

As described above, the E~F section of the photo current signal has the form of a transient curve for the following reason, which will be described with reference to FIG. 3. FIG. 3 illustrates a process of capturing and emitting the carriers as well as the carriers captured in the trap.

In a perfect crystal that has no crystalline defect and has atoms arranged periodically therein, a potential based on the position also has the shape of a periodical function. However, periodicity of the electric potential is broken where there is a crystalline defect, and such a distortion of potential forms traps for charged particles. Such traps forms a deep level within the crystal, and variables of the deep level are explained through the processes of recombination and generation of the carriers, namely, the processes of electron capture, electron emission, hole capture and hole emission (see (a) of FIG. 3).

The electron emission is a process of emitting an electron to a conduction band after the electron that has been in the trap gains energy, as shown in (a) of FIG. 3, and the electron capture is a process of capturing an electron that transfers to the trap after the free electron that has been in the conduction band loses energy.

The hole capture, in which the electron that has been in the trap level loses energy and transfers to a valence band, is a process of the trap capturing a hole, as shown in (a) of FIG. 3, and the hole emission, in which the electron having been in the valence band gains energy and is excited to the trap level, is a process of the trap emitting the hole. In any trap, the above 4 processes occur at the same time, and the concentration of free electrons is increased in the electron emission process, in which the electrons captured in the trap gain energy and are excited to the conduction band, and decreased in the electron capture process of the trap, in which the free electrons lose energy and transfer to the trap level.

In (b) of FIG. 3, $E_c$ indicates the energy level of the conduction band, and $E_v$ indicates the energy level of the valence band, and $E_t$ indicates the energy level of the trap, and $\Delta E_t$ indicates activation energy required for the electron captured in the trap level to be excited to the conduction band and function as the free electron. Moreover, n refers to the concentration of the free electrons in the conduction band, and $n_t$ and $p_t$ refer to the concentration of the trap having captures the electron and the hole, respectively. $N_t$ refers to the trap density.

Therefore, in the case that the defective charge trap is positioned in an energy level of the EL sample, it is possible to decrease the concentration of free electrons to be used for emitting EL through the electron-hole recombination process. This is because some of the electrons that would have transferred to the valence band are captured in the trap. As such, if some electrons that have been captured in the trap become to belatedly play the role of the free electrons by gaining the activation energy through the electron emission process, said some electrons generate the transient section, such as the E~F section shown in (b) of FIG. 3. Therefore, by knowing the activation energy ($\Delta E_t$) required for excitation from the trap level to the conduction band, it is possible to verify the energy level ($E_t$) in which the trap is positioned.

Hereinafter, a method for obtaining information (i.e., activation energy, trap level, cross-sectional capture area of trap, trap concentration, etc.) on the defective charge trap that is present in the EL sample will be described with reference to FIG. 4.

Figure 4:
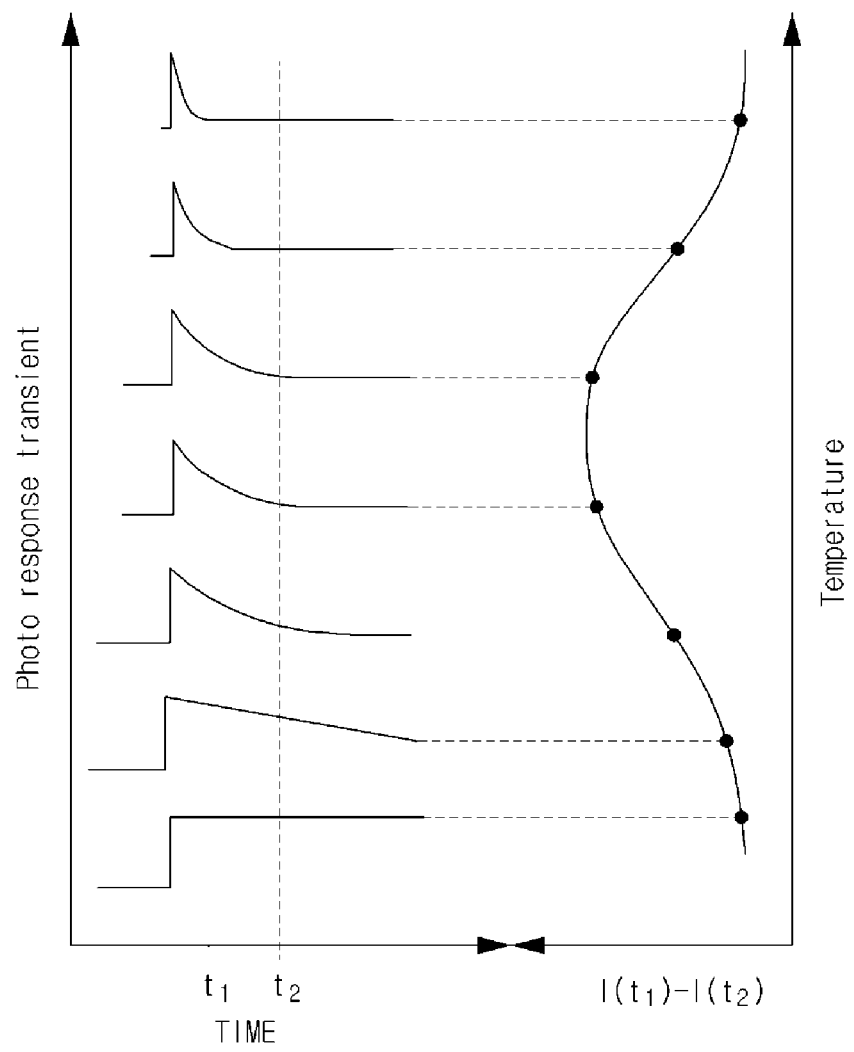
FIG. 4 illustrates a correlation of transient change of a light-receiving signal according to temperature change and a method of obtaining defective charge trap information through this.

FIG. 4 illustrates a correlation of change in transient sections of a light-receiving signal according to temperature change and a method of obtaining defective charge trap information through this.

In the present invention, the defective charge trap information that is present in an EL sample can be obtained by prompting temperature change in the EL sample and then analyzing a change in the transient sections of the light-receiving signal obtained by the EL detector 140 pursuant to the temperature change.

That is, as shown in FIG. 4, the analysis unit 180 of the EL sample analysis apparatus can obtain the information on the defective charge trap by sampling two time points ($t_1$, $t_2$) in a transient section of the light-receiving signal, calculating a difference ($I(t_1)-I(t_2)$) of the light-receiving signal at the two sampled time points, and then using a relation of change in the difference of the light-receiving signal according to the temperature change.

For instance, as shown in FIG. 4, by measuring the photo current signal the time point $t_1$ and the time point $t_2$, the ELTS signal can be obtained with the following equation.

$$I_n(T)=[i(t_1)-i(t_2)]/K(T)$$

$$I_n(T)=e_n[\exp(-e_n t_1)-\exp(-e_n t_2)]$$

with $K(T)=q\mu_n A\tau_n E(N_t+e_n/\beta_n)$ [Equation 1]

Here, $e_n$ is an emission rate (rate window, sec-1); q is a quantity of electric charge of an electron; $\mu_n$ is a mobility of an electron; A is an effective cross-section of a sample; E is an applied electric field; $\tau_n$ is a relaxation time; and $N_t$ is a trap density. By using the condition of $dI_n/d_t=0$ from [Equation 1], the relation between the sampling time and the emission rate at a maximum ELTS signal location can be obtained as follows.

$$\exp[-e_n(t_2-t_1)]=(1-e_nt_1)/(1-e_nt_2) \quad \text{[Equation 2]}$$

Here, the emission rate ($e_n$) is given as [Equation 3] shown below according to the temperature.

$$e_n = A\sigma_T T^2 \exp(-E_t/kT) \quad \text{[Equation 3]}$$

From the above [Equation 3], the activation energy ($\Delta E_t$) and the capture cross-section ($\sigma_T$) of the trap can be obtained.

That is, the relation of change in the difference of the light-receiving signal according to the temperature change as the form of an Arrhenius plot having a Gaussian distribution according to the temperature change, as shown in FIG. 4, and thus, by drawing the Arrhenius plot, the activation energy ($\Delta E_t$) of the trap can be obtained from the slope of the line, and the capture cross-section ($\sigma_T$) of the trap can be also obtained.

EL Lifetime Analysis Apparatus

In the light emitted in a solar cell or an LED device, a luminous gain generated when the applied charge carrier is trapped by the trap and impurities is significantly reduced by the trap and impurities. Therefore, an analysis of lifetime ($\tau$) of a minority carrier in a material can be a method for evaluating whether crystalline materials can be used as the PV (photovoltaic) material.

Figure 5:
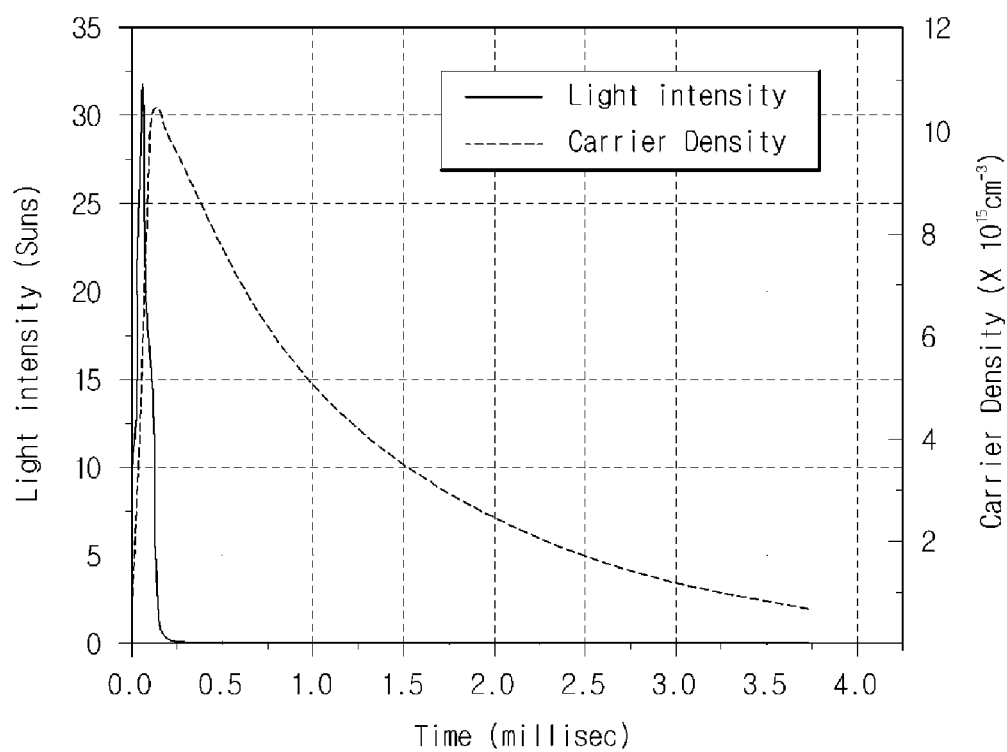
FIG. 5 illustrates the exponential change of carrier density according to light received by a solar cell.

For this, the analysis unit 180 of the EL sample analysis apparatus in accordance with the present invention obtains the information on lifetime of the minority carrier by analyzing the transient sections of the light-receiving signal obtained at a fixed temperature. Here, the charge density of the minority carrier changes exponentially, as shown in FIG. 5, and the transient sections of the light-receiving signal represents the electric property of the minority carrier, and thus the information on the lifetime of the minority carrier can be obtained by calculating a time constant of the transient sections that changes exponentially.

That is, in the present invention, the lifetime of minority carrier, which is one of the indicators of apparatus quality of an EL sample, such as a solar cell, LED, etc., and affects its efficiency, is measured through the ELTS analysis apparatus. In a method of measuring the lifetime of solar cell and LED through this apparatus, the lifetime of the minority carrier and trap, which is exponentially decreased with time, is analyzed by analyzing the transient sections from the response function (current, voltage or capacitance) signal obtained through the EL detector from the EL emitted from a semiconductor sample by applying the pulse type of driving signal to the sample.

Figure 6:
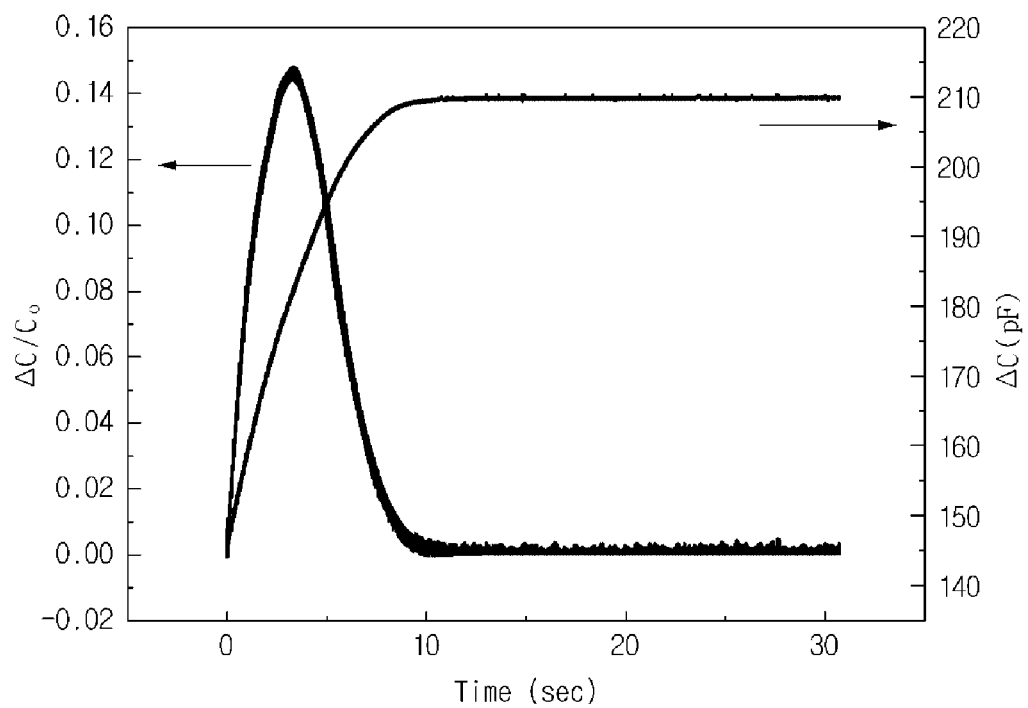
FIG. 6 illustrates a method of analyzing a lifetime based on transient sections that decrease exponentially with time through Optical ICTS (Isothermal Capacitance Transient Spectroscopy).

Moreover, the lifetime can be analyzed by measuring the time division sections for electrostatic capacity among the response functions of the light at a particular temperature. In other words, the lifetime, which is exponentially decreased with time, according to the transient sections is analyzed through optical ICTS (Isothermal Capacitance Transient Spectroscopy) (see FIG. 6). The equation for this is as follows.

$$S(t_i \sqrt{K}, T) = [C(Kt_i) - C(t_i)]/\ln K$$

$$C(t_i) = \Delta C(t_i)/C_0$$
$$= (N_t/2N_A)[e_p^0/(e_n^0 + e_p^0)]\exp[-(e_n^0 + e_p^0)t_i]$$

Here, K is a constant; $N_t$ is the concentration of a trap; $N_A$ is the concentration of an acceptor; $e_p^o$ is an optical hole emission rate; and $e_n^o$ is an optical electron emission rate.

Today, the cell defect and the lifetime for the solar cell and the LED product are measured with separate test instruments. Therefore, with the EL sample analysis apparatus of the present invention, the cell defect and the lifetime for the solar cell and the LED product can be integrally analyzed by a single analysis apparatus, making it possible to save time and cost required for analysis and test.

EL Image Obtaining Apparatus for Analysis of Surface Defect in Micro Units

Moreover, with the configuration illustrated in FIG. 1, the analysis unit 180 of the EL sample analysis apparatus of the present invention can inspect the surface defect of the EL sample 10 in micro units, based on the EL image obtained through the microscope 130 and the photographing device 150.

In other words, the EL sample analysis apparatus of the present invention can be utilized as an apparatus for obtaining a micro EL image for surface defect analysis of an EL sample, such as a solar cell, an LED device and the like, in addition to the above-described ELTS analysis apparatus and EL lifetime analysis apparatus. Accordingly, the EL image emitted from the solar cell or the LED device can be photographed in micro units, making it possible to detect the surface defect and minute external defect of the solar cell or the LED device more precisely.

While the present invention has been described with reference to a certain embodiment, the embodiment is for illustrative purposes only and shall not limit the invention. It is to be appreciated that those skilled in the art can change or modify the embodiment without departing from the scope and spirit of the invention.

What is claimed is:

1. An apparatus for analysis of an electroluminescence sample comprising:
    a pulse generator configured for applying a pulse driving signal to the electroluminescence sample;
    an electroluminescence (EL) detector configured for acquiring a light-receiving signal by receiving electroluminescence emitted from the electroluminescence sample as a result of application of the pulse driving signal, wherein the light-receiving signal obtained by the EL detector is one of a photo current signal, a photo voltage signal and a capacitance signal;
    a temperature controller configured for varying the temperature of the electroluminescence sample; and
    an electroluminescence transient spectroscopy (ELTS) analysis unit configured for acquiring information on a defective charge trap existing in the electroluminescence sample by analyzing a change in a transient section of the light-receiving signal according to a temperature change of the electroluminescence sample, wherein the ELTS analysis unit is configured for obtaining at least one of information on an activation energy level of the defective charge trap, a concentration of the defective charge trap and a capture cross-section of the defective charge trap by sampling two time points in the transient section of the light-receiving signal, calculating a difference of the light-receiving signal at the two sampled time points, and using a relation of change in the difference of the light-receiving signal according to the temperature change.

2. The apparatus of claim 1, wherein the pulse generator is configured for generating a square wave pulse in correspondence with temperature change of the electroluminescence sample by the temperature controller, and wherein the EL detector is configured for detecting EL emitted from the electroluminescence sample in response to the square wave pulse when the square wave pulse is applied.

3. The apparatus of claim 1, wherein the ELTS analysis unit is configured for further obtaining lifetime information by analyzing the transient section of the light-receiving signal obtained at a fixed temperature, and wherein the lifetime information is at least one of information on a minority carrier and the defective charge trap and can be obtained by calculating a time constant of the transient section that changes exponentially.

4. The apparatus of claim 1, further comprising:

a photographing device configured for obtaining an EL image for EL emitted from the electroluminescence sample; and a surface defect analysis unit configured for analyzing a surface defect of the electroluminescence sample based on the EL image.

5. The apparatus of claim 4, wherein a microscope is positioned in front of the photographing device on an optical path of the EL, and wherein the surface defect analysis unit is configured for analyzing the surface defect of the electroluminescence sample based on the EL image in micro units obtained from the photographing device.

6. The apparatus of claim 5, further comprising an optical separator configured for optical separation in such a way that some of the EL emitted from the electroluminescence sample is inputted to the EL detector and the other is inputted to the microscope.

7. The apparatus of claim 1, further comprising a spectroscope configured for detecting a desired wavelength only or cut off an undesired wavelength of EL light emitted from the electroluminescence sample.

8. An apparatus for analysis of an electroluminescence sample comprising:

a pulse generator configured for applying a pulse driving signal to the electroluminescence sample;

an electroluminescence (EL) detector configured for acquiring a light-receiving signal by receiving electroluminescence emitted from the electroluminescence sample as a result of application of the pulse driving signal;

a temperature controller configured for varying the temperature of the electroluminescence sample; and an electroluminescence transient spectroscopy (ELTS) analysis unit configured for acquiring information on a defective charge trap existing in the electroluminescence sample by analyzing a change in a transient section of the light-receiving signal according to a temperature change of the electroluminescence sample, wherein the ELTS analysis unit is configured for further obtaining lifetime information by analyzing the transient section of the light-receiving signal obtained at a fixed temperature, and wherein the lifetime information is at least one of information on a minority carrier and the defective charge trap and can be obtained by calculating a time constant of the transient section that changes exponentially.

9. The apparatus of claim 8, wherein the pulse generator is configured for generating a square wave pulse in correspondence with temperature change of the electroluminescence sample by the temperature controller, and wherein the EL detector is configured for detecting EL emitted from the electroluminescence sample in response to the square wave pulse when the square wave pulse is applied.

10. The apparatus of claim 8, further comprising:

a photographing device configured for obtaining an EL image for EL emitted from the electroluminescence sample; and a surface defect analysis unit configured for analyzing a surface defect of the electroluminescence sample based on the EL image.

11. The apparatus of claim 10, wherein a microscope is positioned in front of the photographing device on an optical path of the EL, and wherein the surface defect analysis unit is configured for analyzing the surface defect of the electroluminescence sample based on the EL image in micro units obtained from the photographing device.

12. The apparatus of claim 11, further comprising an optical separator configured for optical separation in such a way that some of the EL emitted from the electroluminescence sample is inputted to the EL detector and the other is inputted to the microscope.

13. The apparatus of claim 8, further comprising a spectroscope configured for detecting a desired wavelength only or cut off an undesired wavelength of EL light emitted from the electroluminescence sample.

* * * * *